United States Patent [19]

Sedgwick

[11] Patent Number: 4,528,690
[45] Date of Patent: Jul. 9, 1985

[54] COMPACT HYBRID STETHOSCOPE

[75] Inventor: Jim Sedgwick, Scarsdale, N.Y.

[73] Assignee: Genovation, Inc., Glen Cove, N.Y.

[21] Appl. No.: 588,767

[22] Filed: Mar. 12, 1984

[51] Int. Cl.³ .......................... H04R 1/46; A61B 5/02
[52] U.S. Cl. ...................................... 381/67; 128/715
[58] Field of Search ................... 381/67; 181/126, 131; 128/715

[56] References Cited

U.S. PATENT DOCUMENTS

| | | | |
|---|---|---|---|
| 3,182,129 | 5/1965 | Clark et al. | 128/715 |
| 3,247,324 | 4/1966 | Cefaly et al. | 381/67 |
| 3,525,810 | 8/1970 | Adler | 381/67 |
| 3,690,404 | 9/1972 | Collins | 181/131 |
| 3,846,585 | 11/1974 | Slosberg et al. | 381/67 |
| 4,010,335 | 3/1977 | Yasuda | 381/26 |
| 4,037,064 | 7/1977 | Yasuda | 381/26 |
| 4,052,979 | 10/1977 | Scherr et al. | 128/690 |
| 4,064,965 | 12/1977 | Brown | 181/131 |
| 4,272,650 | 6/1981 | Bolgiano et al. | 179/77 |
| 4,409,687 | 10/1983 | Berti et al. | 179/2 EB |
| 4,438,771 | 3/1984 | Friesen et al. | 128/721 |

FOREIGN PATENT DOCUMENTS

| | | | |
|---|---|---|---|
| 1267378 | 5/1968 | Fed. Rep. of Germany | 128/715 |
| 2453926 | 5/1976 | Fed. Rep. of Germany | 128/715 |

Primary Examiner—Gene Z. Rubinson
Assistant Examiner—Danita R. Byrd
Attorney, Agent, or Firm—Yusuke Takeuchi

[57] ABSTRACT

A compact hybrid stethoscope comprises a detachable headpiece for picking up auscultory sounds, a flexible tubing pneumatically connected to the headpiece for transmitting the auscultory sounds, an amplifier unit pneumatically connected to the flexible tube for receiving the auscultory sounds and reproducing amplified auscultory sounds, and a pair of auricles pneumatically connected to the amplifier for transmitting the reproduced sounds to the user's ears. An automatic on/off timer switch is connected to the amplifier so that even if inadvertently left on, the on/off timer automatically switches off the hybrid stethoscope after a predetermined interval, thus saving electric power. A tone control is connected to the amplifier so that the user may listen to the particularly desired auscultory sounds, such as respiratory or cardiac sounds while eliminating certain other auscultory sounds. A volume control is connected to the amplifier so that at the minimum volume the hybrid stethoscope works as a traditional acoustic stethoscope while at the maximum volume it enables a user to hear auscultory sounds through several layers of cloth in a noisy room.

3 Claims, 4 Drawing Figures

COMPACT HYBRID STETHOSCOPE

BACKGROUND OF THE INVENTION

1. Field of the Invention

The present invention relates generally to medical and laboratory equipment, and more particularly to a new compact hybrid stethoscope that combines a traditional acoustic stethoscope and a sophisticated electronic stethoscope.

2. Description of the Prior Art

For many years, acoustic stethoscopes have been commonly used by doctors and nurses in ausculation; i.e., listening to sounds made within the body to diagnose any abnormal condition present in the body. Electronic stethoscopes were introduced thereafter to isolate and make audible auscultory sounds to make diagnosis easier. One of such electronic stethoscopes is described in U.S. Pat. No. 3,525,810 to Alan John Adler. The electronic stethoscope of the Adler patent is directed to detecting the stenosis- induced sounds. The stenosis is a narrowing of the diameter of a body tube, and its sounds have an exceedingly low intensity and a close relationship to the ordinary heart sounds. It is made up of a sophisticated microphone, a preamplifier, a band-pass filter, an output amplifier, and a headphone.

My investigation has revealed that doctors and nurses want their stethoscopes to look, feel, and operate like the traditional acoustic stethoscopes with which they are familia, while permitting them to listen to auscultory sounds with greater volume and clarity than previously possible with other portable stethoscopes. It also has been shown that doctors and nurses are so busy that they tend to forget to turn off the electronic stethoscope after each use. A dead battery often results, rendering the electronic stethoscope inoperable when needed, and making the doctor embarassed and reluctant to again use an electronic stethoscope.

SUMMARY OF THE INVENTION

Accordingly, it is an object of the invention to provide a compact hybrid stethoscope that has the capacity of a traditional acoustic stethoscope yet is capable of reproducing auscultory sounds with greater volume and clarity.

Another object of the invention is to provide a compact hybrid stethoscope that promotes long battery life even in the event of a user inadvertently forgetting to switch off the stethoscope.

Still another object of the invention is to provide a compact hybrid stethoscope with which the user may listen to the desired sounds while eliminating undesired sounds.

Yet another object of the invention is to provide a compact hybrid stethoscope with which the user may compare received auscultory sounds with the sounds which he would hear with a traditional acoustic stethoscope.

According to the invention there is provided a compact electronic stethoscope which comprises a headpiece for picking up sounds, a flexible tubing pneumatically connected at one end to the headpiece for transmitting the acoustic sounds, an amplifier unit consisting mainly of a microphone pneumatically connected to the other end of the flexible tube for converting the acoustic sounds into electric signals, an amplifier electrically connected to the microphone for amplifying the electric signals, a speaker electrically connected to the amplifier for converting the amplified electric signals to acoustic sounds, and a pair of auricles pneumatically connected to the speaker for transmitting the sounds to the user's ears. Since the headpiece, flexible tubing and auricles are used for the hybrid stethoscope, the user may use it in the same manner and with the same feeling as when the traditional acoustic stethoscope. In addition, the stethoscope may be folded up and carried in a doctor's pocket.

According to another aspect of the invention the compact hybrid stethoscope is provided with an automatic on/off timer connected to the amplifier so that even if inadvertently left on, the on/off timer automatically turns off the stethoscope after a predetermined interval, thus saving electric power.

According to still another aspect of the invention the compact hybrid stethoscope is provided with a tone control or filter connected to the amplifier so that the user may listen to the particularly desired auscultory sounds, such as respiratory or cardiac sounds while eliminating certain other auscultatory sounds.

According to yet another aspect of the invention the compact hybrid stethoscope is provided with a volume control connected to the amplifier so that at the minimum volume the user may compare it with the sound at which he would listen to with the traditional acoustic stethoscope.

Other objects, structures, functions and advantages of the invention will be apparent from the following description of the preferred embodiments with reference to the accompanying drawings.

DESCRIPTION OF THE PREFERRED EMBODIDMENTS

Figure 1:
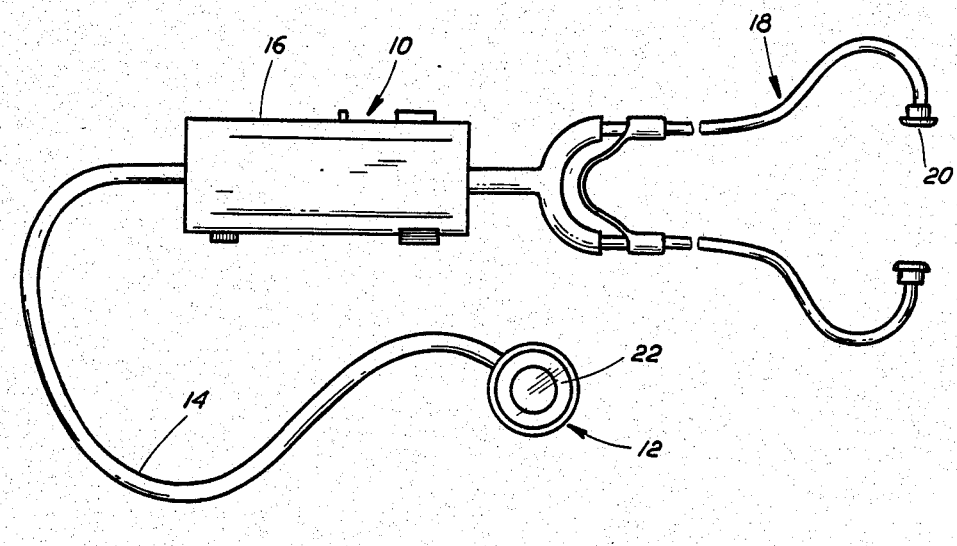
FIG. 1 is a top view of a hybrid stethoscope embodying the present invention.

Referring now to FIG. 1, there is shown a hybrid stethoscope generally designated 10, embodying the present invention. The hybrid stethoscope 10 includes a headpiece or sound pickup 12 designed to be held against the patient's body for picking up, for example, patient's heartbeat. A flexible tube 14 is pneumatically connected at one end to headpiece 12 for transmitting the heartbeat. An amplifier unit 16, which is pneumatically connected to the other end of flexible tube 14, electronically amplifies the heartbeat. A pair of auricles 18 join together at one end to form a Y-shape headset. The stem portion of the auricles is pneumatically connected to the amplifier unit 16 and the branch ends are provided with earpieces 20 and are designed to be placed in the user's ears for listening to the heartbeat.

The preferred headpiece 12 is a standard unit with a membrane 22 that, when held against the patient's body, vibrates to produce sound waves. This type of headpiece is commonly used on traditional acoustic stethoscopes. Consequently the doctor feels comfortable in use of the present device and makes use of the experience acquired with traditional acoustic stethoscopes for diagnosis. Headpiece 12 is preferably made detachable from the flexible tube 14 so that the user may easily remove and replace it with any other head of his choice that is most suitable in terms of shape, size, and weight for the patient's body or particular ailment to be diagnosed. The preferred flexible tube 12 is made of rubber and connects the headpiece 12 to the amplifier unit 16 to form a pneumatic system. Another flexible tube may be used between the amplifier unit 16 and the auricles 18 to form another pneumatic system with the auricles.

Figure 2:
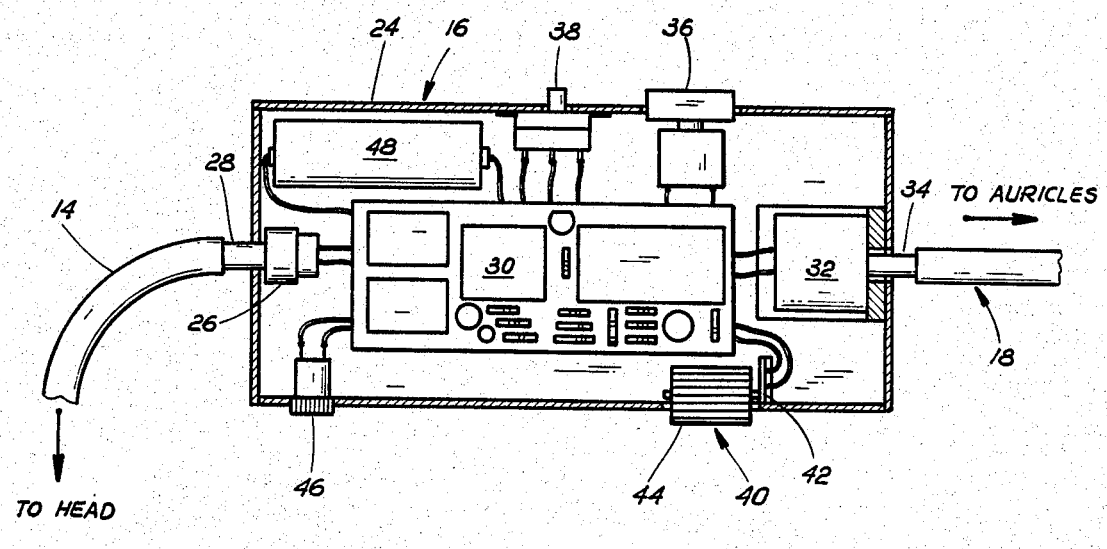
FIG. 2 is a top view of an amplifier unit, with its top cover removed, of the hybrid stethoscope of FIG. 1.

The amplifier unit 16 is illustrated in more detail in FIG. 2, having its top cover removed to show its inside construction. The unit 16 includes a case 24 that is approximately the size of a pack of cigarettes and composed of, for example, a plastic material. A microphone 26 is mounted on the left-hand side of case 24 and is pneumatically connected to the rubber tube 14 through a short metal pipe 28. The preferred microphone 26 is of the electret type which has its own field effect transistor amplifier (FET). Electrically connected to microphone 26 is a printed circuit board 30 that is mounted substantially in the center of case 24 and supports various electronic parts in such a configuration as described below. A speaker 32 is mounted on the right-hand side of case 24 and is electrically connected to the output of p.c. board 30. The preferred speaker 32 is a dynamic microphone used as a speaker and is connected through a short metal pipe 34 to the auricles so as to form a closed pneumatic system.

An on/off switch 36, preferably of the small two-prong, push-button type, is mounted on the right upper side of case 24 and is electrically connected to the p.c. board 30. A high/low tone switch 38, preferably of the small three-prong, slide type, is mounted on the central upper side of case 24 and is electrically connected to the p.c. board 30. A volume control 40 is mounted on the right lower side of case 24 and is electrically connected to the p.c. board 30. The preferred volume control 40 consists mainly of a variable resistor 42 and a knob 44 rotatable to adjust the resistance. An auxiliary output 46 is mounted on the left lower side of case 24. The preferred auxiliary output 46 is a standard jack commonly used to plug in an auxiliary amplifier or taperecorder. A battery 48 is provided at the upper lefthand corner of case 24 to supply electric power to the p.c. board 30. The preferred battery is a Duracell TR-175 (7 volts).

Figure 3:
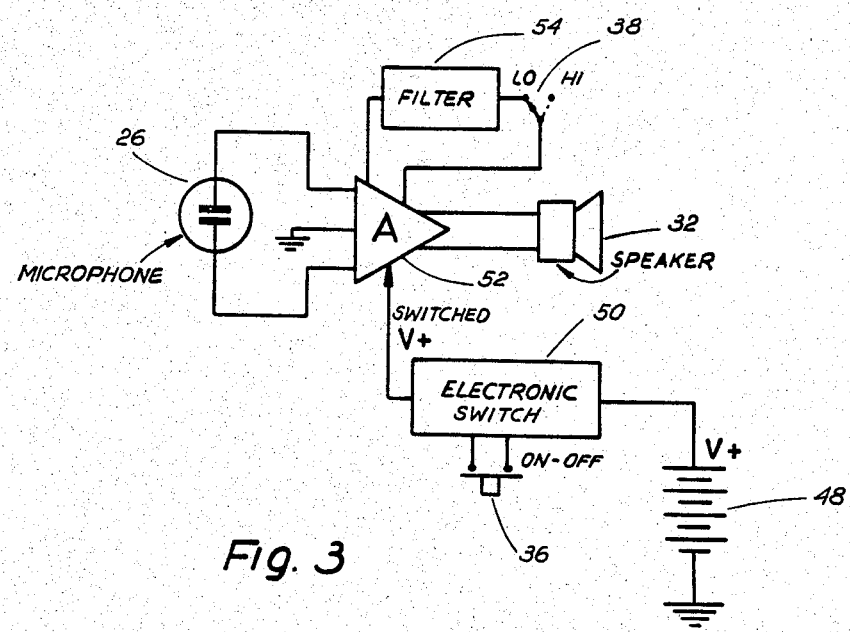
FIG. 3 is a block diagram of the electronic circuitry of the amplifier unit of FIG. 2.

The general electronic circuitry of the amplifier unit 16 is illustrated in the form of a block diagram in FIG. 3. An on/off timer circuit electronic switch 50 is connected to the mike 26 and an amplifier circuit 52 so that when it is in the on state, it supplies them with electric power from the battery. On the other hand, when it is in the off state, it shuts off the electric power supply automatically after a predetermined period of time. The amplifier circuit 52, which is normally a broad-band frequency amplifier, is provided with a high-pass filter circuit 54 through the switch 38 so that it serves as a low-frequency amplifier. The speaker 32 is connected to the output of amplifier circuit 52 for receiving the electric power and supplying acoustic power into the auricles.

Figure 4:
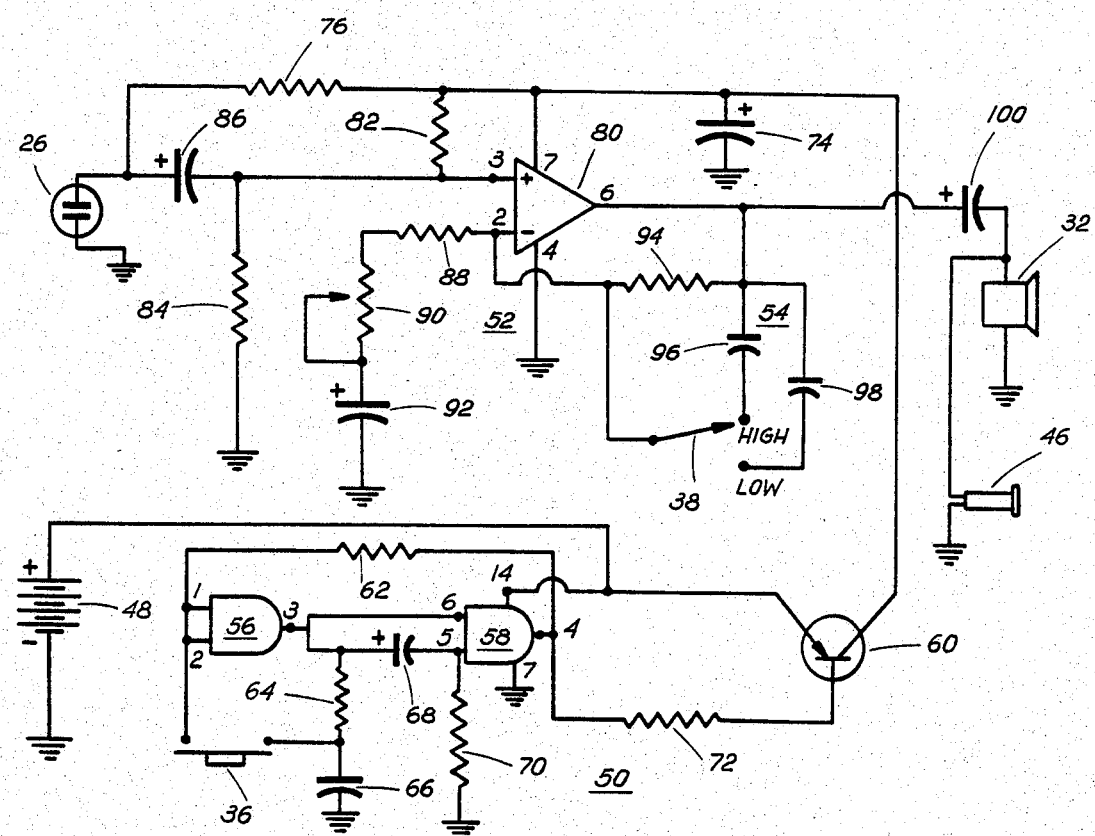
FIG. 4 is a schematic circuit diagram of the amplifier unit of FIG. 2.

Referring now specifically to FIG. 4, the on/off circuit 50 is made up mainly of a Schmitt trigger integrated circuit including two Schmitt triggers 56 and 58, and a transistor 60. The two Schmitt triggers are designed in such a manner that when pin 3 of Schmitt trigger 56 is low, the output of pin 4 of Schmitt trigger 58 is always high. Pin 4 is coupled through a resistor 62 to the gate of Schmitt trigger 56 on pins 1 and 2. Pin 3 is connected in parallel to two series connections of a resistor 64, a capacitor 66, a capacitor 68, and a resistor 70. On the other hand, it is connected to pin 6 of Schmitt trigger 58 through a conductor or hard wire. Pin 5 of Schmitt trigger 58 is connected to the junction of capacitor 68 and resistor 70. The push-button swithch 36 is connected across pin 2 of Schmitt trigger 56, and the junction of resistor 64 and capacitor 66. Pins 14 and 7 of Schmitt trigger 58 are connected to the positive and negative lines of battery 48 respectively. Pins 8, 9, 12, and 13 (not shown) are connected to the negative line of battery 48. The base and emitter of transistor 60 are connected to pin 4 of Schmitt trigger 58 through a resistor 72 and the positive line (+B 7 volts) of battery 48 respectively. The collector of transistor 60 is connected to the negative line of battery 48 through a capacitor 74. The mike 26 is connected across the negative line of battery 48 and the collector of transistor 60 through a resistor 72.

The amplifier circuit 52 is made up mainly of an op amp 80 which has a high impedance FET input. The non-inverting input on pin 3 of the op-amp 80 is connected to the junction of a series connection of two resistors 82 and 84 and to the output of mike 26 through a capacitor 86. The resistors 82 and 84 form a voltage divider to bias the non-inverting input of op amp 80 at a half the supply voltage. Pin 2 of the op-amp is connected to the negative line of battery 48 through a series connection of a fixed resistor 88, a variable resistor 90 and a capacitor 92. Pins 7 and 4 of the op-amp are connected to the collector of transistor 60 and the negative line of battery 48 respectively. Pin 6 of the op-amp is connected to pin 2 through a resistor 94, which together with the resistors 88 and 90 gives the gain of the amplifier stage by the following formula:

$$\text{Gain} = \frac{\text{resistance of } R94}{\text{resistance of } R88 + R90}$$

In the preferred embodiment, the values of these resistors are selected so that the gain varies approximately from 3 to 300 as the variable resistor 90 is changed substantially from maximum to zero resistance.

The filter 54 is comprised primarily of two capacitors 96 and 98 that are selectively connected across the resistor 94 through switch 38. In the figure, the switch 38 is closed on the high-tone side to couple the capacitor 96, the value of which is less than that of the capacitor 98.

The speaker 32 and the external or auxiliary jack 46 are connected across the negative line of battery 48 and pin 6 of the op-amp 80 through a capacitor 100 to complete the circuit of amplifier unit 16. The speaker has a resistance of about 200 ohms.

In operation, the user places auricles 18 in his ears and holds headpiece 12 against the patient's body, just as he would with an ordinary acoustic stethoscope. Since the headpiece is detachable from rubber tube 14, he can choose the most suitable headpiece for the particular purpose from a wide range of standard headpieces.

Then, when he presses the on/off switch 36, the charge on the capacitor 66 is transferred through to pins 1 and 2 of Schmitt trigger 56. In the case when the voltage of pin 3 is low, the charge on the capacitor 66 is zero volts, which causes pins 1 and 2 to be a logic low, or zero. Although the resistor 62 tries to charge up the capacitor 66, there is insufficient time for this to occur before pin 3 goes to high voltage. As pin 3 goes high, the input on pin 6 to the gate of Schmitt trigger 58 immediately goes high since they are hard wired, but also a charge is coupled by the capacitor 68 to pin 5 or the other input of Schmitt trigger 58. This charge now causes both inputs at pins 6 and 5 to be high, which in turn causes pin 4 to be low, thus forward biasing the transistor 60 and switching on the amplifier 52.

The microphone 24 now has its current supplied through the resistor 76, across which the output voltage of microphone 24 is developed. This voltage is then coupled by the capacitor 86 to the non-inverting input at pin 3 of the op-amp 80. The output of op-amp 80 is coupled by the capacitor 100 to the speaker 32 so that the AC may pass through to the speaker while the DC may not pass. The amplifier 52 is de-coupled on its power supply input by the capacitor 74 to bypass the AC to the ground and stabilize the amplifier circuit 52. The speaker forms a closed pneumatic system with the auricles 18 as described above.

The resistor 88 is used in series with volume control resistor 90 so that when volume control resistor 90 is adjusted to the minimum resistance for the maximum volume, the op-amp 80 does not saturate. If this resistor were not present, the amplifier would go into an open loop gain condition, at the minimum resistance of the volume control. The amplifier is capable of increasing the volume level of auscultory sounds so that a patient's heartbeat can be heard even through several layers of clothing in a noisy room. When the volume control 90 is adjusted to the maximum resistance for the minimum volume, this hybrid stethoscope works just as a traditional acoustic stethoscope in the volume level so that the doctor may compare it with the sound he would hear with a traditional stethoscope.

The resistor 94 is a feedback resistor in the op-amp circuit 52 and is normally bypassed by the capacitor 96. This limits some of the high frequencies and causes the frequency response of the amplifier 52 to be optimized for all sounds through to the sounds made by a person while breathing so that the doctor may use this hybrid stethoscope for respiratory measurements. In other words, the capacitor 96 provides high frequency response when the tone control 38 is in the "high" position. When the tone control 38 is switched to the "low" position, the capacitor 98 bypasses all high frequencies to provide low frequency response. In other words, the hybrid stethoscope is optimized for listening to cardiac sounds.

Pin 4, now being low, causes pins 1 and 2 to remain low after the on/off switch is released since the resistor 62 connects pin 4 to pins 1 and 2. At this time, while pin 3 is high, the capacitor 66 is charged through the resistor 64. This stores the information as to which state the switch is in for future on/off depressions of the switch 36. The charge gradually leaks away from the capacitor 68 through the resistor 70 in the interval determined by the values of capacitor 68 and resistor 70 to the level where pin 4 again goes high, thus turning off the transistor 60 and in turn the amplifier 52. In a preferred embodiment, the values of capacitor 68 and resistor 70 are selected so that the interval is two minutes and forty five seconds. This high voltage at pin 4 is coupled by the resistor 62 back to pins 1 and 2.

When, during the interval that the amplifier 52 is still on, the on/off switch 36 is again depressed, the charge on the capacitor 66, which now is logic high, brings pins 1 and 2 high. This causes the output pin 3 to go low, and the instant this happens, pin 4 goes high. This charge is coupled through the resistor 62 back to pins 1 and 2. The transistor 60 and in turn the amplifier 52 are now switched off. Accordingly, depressing the switch 36 repeatedly causes the unit 16 to alternately turn on and off, but if the unit is left on, the capacitor 68 discharges through the resistor 70 and automatically shuts down the unit 16 after 2 minutes 45 seconds.

The resistor 72 is used to couple the output of pin 4 to the base of transistor 60 for limiting current to the base. The quiescent current of the unit 16, with no signal coming into the microphone 26, is about 3 milliamps. When the unit is switched off, the current drain is about one tenth of one microamp. Consequently, a single battery powers the unit for a considerable length of time—at least 50 hours of actual use from one Duracell TR-175 battery.

Finally, for purposes of presenting a specific example of component values in the illustrative circuit, the following may be considered:

| | |
|---|---|
| Schmitt triggers 56 and 58 | CMOS 4093B |
| Transistor 60 | 2N2907A |
| Resistor 62 | 4.7K ohms |
| Resistor 64 | 220K ohms |
| Capacitor 66 | 0.047 microfarads |
| Capacitor 68 | 47 microfarads |
| Resistor 70 | 3.3 meg ohms |
| Resistor 72 | 22K ohms |
| Capacitor 74 | 220 microfarads |
| Resistor 76 | 2.2K ohms |
| Op-amp 80 | T.I. TL091 |
| Resistor 82 | 22K ohms |
| Resistor 84 | 22K ohms |
| Capacitor 86 | 10 microfarads |
| Resistor 88 | 470 ohms |
| Variable resistor 90 | 47K ohms |
| Capacitor 92 | 1 microfarads |
| Resistor 94 | 150K ohms |
| Capacitor 96 | 0.002 microfarads |
| Capacitor 98 | 0.01 microfarads |
| Capacitor 100 | 220 microfarads |

It is thought that the hybrid stethoscope of the present invention will be understood from the foregoing description and it will be apparent that various changes may be made in the form, construction and arrangement of the parts thereof without departing from the spirit and scope of the invention.

What is claimed is:

1. A compact hybrid stethoscope for use in auscultation of sounds made within the body, which comprises:
    (a) a sound pickup to be held against said body for picking up said sounds;
    (b) tubing means pneumatically connected at one end to said sound pickup for transmitting said sounds;
    (c) amplifying means which includes:
        (i) a microphone pneumatically connected to the other end of said tubing means for converting said sounds into electric signals;
        (ii) an amplifier circuit electrically connected to said microphone for amplifying said electric signals;
        (iii) an electronic switch connected between said amplifier circuit and a battery, said electronic switch including:
        a pair of CMOS schmitt triggers connected across said battery so as to be powered at all times; and
        an on/off switch connected to one of said schmitt triggers so that said electronic switch may shut off said amplifier circuit a predetermined period of time after said on/off switch is pressed, and (iv) a speaker electrically connected to said amplifier circuit for converting said electric signals into acoustic sounds; and
(d) a head set pneumatically connected to said speaker for transmitting said sounds to the user's ears.

2. A compact hybrid stethoscope as defined in claim 1, wherein said amplifying means further includes an external jack connected in parallel to said speaker to the output of said amplifying circuit for plugging in an auxiliary amplifier or taperecorder for storing auscultory sounds on tape.

3. A compact hybrid stethoscope as defined in claim 2, wherein said microphone and said speaker are directly connected to said tubing means and said head set respectively.

* * * * *